(12) United States Patent
Okada

(10) Patent No.: US 8,724,112 B2
(45) Date of Patent: May 13, 2014

(54) LASER GAS ANALYSIS APPARATUS

(75) Inventor: Masanori Okada, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 104 days.

(21) Appl. No.: 13/553,943

(22) Filed: Jul. 20, 2012

(65) Prior Publication Data

US 2013/0021612 A1 Jan. 24, 2013

(30) Foreign Application Priority Data

Jul. 21, 2011 (JP) .................................. 2011-159834

(51) Int. Cl.
*G01N 21/00* (2006.01)
(52) U.S. Cl.
USPC .......................................................... 356/437
(58) Field of Classification Search
None
See application file for complete search history.

(56) References Cited

U.S. PATENT DOCUMENTS 6,345,234 B1 * 2/2002 Dilger et al. ..................... 702/24

FOREIGN PATENT DOCUMENTS

| JP | 58-124932 A | 7/1983 |
|----|-------------|--------|
| JP | 03-295446 A | 12/1991 |
| JP | 2010-032422 A | 2/2010 |

OTHER PUBLICATIONS

Tamura, et al., "TDLS200 Tunable Diode Laser Gas Analyzer and its Application to Industrial Process", Yokogawa Technical Report, Yokogawa Electric Corporation, 2010, vol. 53, No. 2 (2010), p. 51-54 Abstract.
European Search Report dated Dec. 6, 2012 issued by the European Patent Office in corresponding European Patent Application No. 12177265.1.
Werle, et al., "Signal processing and calibration procedures for in situ diode-laser absorption spectroscopy", Spectrochimica Acta Part A, 2004, vol. 60, No. 8-9, pp. 1685-1705, XP55045463.
Khaidukov, et al., "Observation of Time-transient spectral narrowing at 309 nm in $Ce^{3+}$ doped $SrF_2$ crystal", Optics Communication, 2002, vol. 205, No. 4-6, pp. 415-420, XP004353463.
Xia, et al., "Automatic Gain Control Method Based on Tumble Diode Laser Used for Ambient Trace-gas Monitoring", Electrical and Control Engineering (ICECE), 2010, pp. 521-523, XP031796127.

* cited by examiner

Primary Examiner — Gordon J Stock, Jr.
(74) Attorney, Agent, or Firm — Sughrue Mion, PLLC

(57) ABSTRACT

A timing generating circuit outputs, to a laser controller, a change pulse signal for changing an oscillation wavelength of the laser beam, and outputs, to a data acquisition circuit, a timing pulse signal for outputting data to a processor. An edge detection circuit detects an edge of a measurement signal outputted from a detector circuit. A delay measuring circuit receives a change pulse signal outputted from the timing generating circuit, receives an edge detection signal outputted from the edge detection circuit, and measures a delay of a time for which the laser beam with an oscillation wavelength changed based on the change pulse signal reaches the detector circuit after the change pulse signal is outputted from the timing generating circuit. The timing generating circuit delays a time for outputting data from the data acquisition circuit to the processor based on the delay of time outputted from the delay measuring circuit.

2 Claims, 4 Drawing Sheets

LASER GAS ANALYSIS APPARATUS

CROSS-REFERENCE TO RELATED APPLICATION(S)

The present application claims the benefit of priority of Japanese Patent Application No. 2011459834, filed on Jul. 21, 2011, the contents of which are incorporated herein by reference.

BACKGROUND

1. Technical Field

The present disclosure relates to a laser gas analysis apparatus. Particularly, it relates to a laser gas analysis apparatus which eliminates a signal transmission delay varying depending on an installation environment to thereby improve the accuracy of measurement.

2. Related Art

A laser gas analyzer using a TDLAS (Tunable Diode Laser Absorption Spectroscopy) method has an advantage in that the laser gas analyzer can measure high-temperature or the concentration of a target component to be measured such as corrosive gas or the like in a non-contact manner at a high speed in real time with a high component selectivity without being interfered by other components by only irradiating the target to be measured with laser beam from a tunable diode laser.

FIG. 3 is a block diagram showing a related-art laser gas analysis apparatus using the TDLAS method. The laser gas analysis apparatus is constituted by a light source unit including a semiconductor laser for emitting a laser beam into a process gas atmosphere, and a detection unit including a light receiving element for detecting the laser beam transmitted through a measurement space in the process gas atmosphere and an arithmetic processor for processing an output signal of the light receiving element.

In the laser gas analysis apparatus shown in FIG. 3, an optical absorption spectrum peculiar to molecules of a to-be-measured target component in the range of from an infrared region to a near-infrared region based on vibration and rotation energy transition of the molecules is measured by use of a semiconductor laser having an extremely narrow spectral linewidth of an oscillation wavelength. The most of molecules including $O_2$, $NH_3$, $H_2O$, $CO$, $CO_2$, etc. have molecule-specific absorption spectra in the range of from the infrared region to the near-infrared region. The concentration of a target component can be calculated when the optical absorption quantity (absorbance) in a specific wavelength is measured.

In FIG. 3, a diode laser 11 provided as a semiconductor laser in a light source unit 10 emits a laser beam into an atmosphere of process gas 20. The laser beam outputted by the diode laser 11 has an extremely narrow spectral linewidth of an oscillation wavelength. The oscillation wavelength can be changed by changing the laser temperature or the driving current. Thus, only one of absorption peaks in the absorption spectra can be measured.

Accordingly, an absorption peak which has not been affected by interference gas can be selected so that high wavelength selectivity can be obtained without being affected by other interference components. It is therefore possible to measure the process gas directly without removing the interference gas in a stage prior to the measurement.

When the oscillation wavelength of the diode laser 11 is changed near one absorption line of a component to be measured, a spectrum can be measured correctly without overlapping with any other interference component. However, the shape of the spectrum changes in accordance with a broadening phenomenon of the spectrum caused by the process gas temperature, the process gas pressure, coexisting gas components, etc. It is therefore necessary to correct the spectrum in actual process measurement accompanied by those environmental fluctuations.

To this end, the apparatus in FIG. 3 uses a spectrum area method in which while the oscillation wavelength of the diode laser 11 is changed, an absorption spectrum is measured to obtain the area of the spectrum, and the area of the spectrum is converted into component concentration.

Another laser gas analysis apparatus uses a peak height method in which a component to be measured is obtained from the height of a peak of an absorption spectrum or a 2f method in which a wavelength changing signal is modulated and the concentration of a component to be measured is obtained front a P-P (Peak to Peak) value of a waveform modulated with a frequency twice as high as the frequency of the signal. These methods are apt to be greatly affected by fluctuations of temperature, pressure, coexisting gas components, etc.

On the other hand, in principle, the spectrum area method is a method not affected by any change caused by a difference in coexisting gas components (the area of a spectrum is substantially fixed regardless of the coexisting gas components). The spectrum area method exhibits a linear change with respect to the fluctuation of pressure in principle.

In the peak height method or the 2f method, all the three fluctuation factors (temperature, pressure and coexisting gas components) have nonlinear influence. Correction is difficult when these fluctuation factors coexist. According to the spectrum area method, however, linear correction for the fluctuation of gas pressure and nonlinear correction for the fluctuation of gas temperature can be performed to achieve accurate correction.

The laser beam transmitted through the atmosphere of the process gas 20 is received by a light receiving element 31 as a constituent component of a detector circuit 40 which is provided in a detection unit 30. The received laser beam is converted into an electric signal.

An output signal of the light receiving element 31 is adjusted to a suitable amplitude level by a variable gain amplifier 32, and inputted to an converter 33, in which the resulting signal is converted into a digital signal.

In sync with change of the oscillation wavelength of the diode laser 11, output data of the A/D converter 33 are integrated in an integrator 34 and stored into a memory 35 a predetermined number of times (for example, several hundred times to several thousand times) repeatedly between the integrator 34 and the memory 35 as constituent components of a data acquisition circuit (hereinafter referred to as DAQ circuit) 41. Therefore, noise contained in the measurement signal is removed in order to smooth the data. The measurement signal is then inputted to a CPU 36.

The CPU 36 performs an arithmetic process for analysis of the concentration of the process gas etc. based on the measurement signal from which the noise has been removed. In addition, the CPU 36 also adjusts the gain of the variable gain amplifier 32 when the amplitude level of the output signal of the light receiving element 31 is not suitable as an input level to the A/D converter 33.

A timing generating circuit 42 outputs, to a laser controller 43, a change pulse signal for changing the oscillation wavelength of laser beam to be emitted from the diode laser, and outputs, to the integrator 34, a timing pulse signal for receiving an output from the A/D converter 33.

Non-Patent Document 1 has disclosed measurement principles, features and specific measurement examples of a laser gas analyzer using tunable diode laser absorption spectroscopy.

PRIOR TECHNICAL DOCUMENT

Patent Document

[Non-Patent Document 1] Kazuto Tamura and other three, "TDLS200 Tunable Diode Laser Gas Analyzer and its Application to Industrial Process", Yokogawa Technical Report, Yokogawa Electric Corporation, 2010, Vol. 53, No. 2 (2010), p. 51-54

FIGS. 4A and 4B are graphs showing a timing sequence of the related-art laser gas analysis apparatus. The vertical axis designates signal intensity, and the horizontal axis designates time.

In FIG. 4A, a solid line (i) designates a change of intensity in the laser output (output of diode laser), and a broken line (ii) designates a measurement signal inputted to the DAQ circuit. A solid line (iii) designates a change pulse signal outputted from the timing generating circuit 42, that is, a timing for generating a change pulse signal in the timing generating circuit 42. A broken line (iv) designates the change pulse signal inputted to the laser controller 43 through a sync cable 44, and indicates that a delay T1 of a time for which the oscillation wavelength of the laser beam is changed after the change pulse signal is outputted from the timing generating circuit 42 occurs. Recesses (v) expressed in the broken line (ii) designate wavelength portions absorbed by the process gas.

The laser beam emitted from the light source unit 10 and transmitted through the process gas is inputted to the DAQ circuit 41 through the light receiving element 31, the variable gain amplifier 32 and the A/D converter 33 constituting the detector circuit 40. However, a delay T2 occurs after the change pulse signal generated by the timing generating circuit 42 is inputted to the laser controller 43 to change the oscillation wavelength of the laser beam emitted from the diode laser and before the laser beam with the changed oscillation wavelength transmitted through the process gas and converted into an electric signal is inputted to the DAQ circuit 41. Thus, there occurs a total delay TD as the sum of the delay T2 and the delay T1.

FIG. 4B shows the relationship between a wavelength (vi) indicating a change of intensity in the laser output (output of diode laser) on the assumption that the laser oscillates without occurrence of any delay relative to the change pulse signal generated by the timing generating circuit 42 (i.e., without occurrence of the time delay T1) and a signal (vii) inputted to the DAQ circuit 41 with occurrence of the time delay TD.

The delays T1 and T2 are values different from one process to another in accordance with the length of a sync cable or the installation state of a process. It is therefore difficult to set a timing of generating the change pulse signal in consideration of the delays T1 and T2 estimated in advance.

Such delays cause the lowering of accuracy when the state of the process gas is analyzed by the CPU 36 disposed in a subsequent stage.

SUMMARY

One or more exemplary embodiments of the present invention provide a laser gas analysis apparatus which measures and cancels a total delay of a system including delays which are caused by user's environment but can hardly be estimated in advance.

A laser gas analysis apparatus according to an exemplary embodiment of the invention, comprises:

a light source unit including a semiconductor laser configured to emit a laser beam into process gas and a laser controller configured to control an oscillation wavelength of the laser beam;

a detector circuit configured to detect the laser beam transmitted through the process gas;

a data acquisition circuit configured to receive a measurement signal outputted from the detector circuit and to remove noise contained in the measurement signal;

a processor configured to receive data outputted from the data acquisition circuit and to compute concentration of the process gas;

a timing generating circuit configured to output, to the laser controller, a change pulse signal for changing the oscillation wavelength of the laser beam and to output, to the data acquisition circuit, a timing pulse signal for outputting data to the processor;

an edge detection circuit configured to detect an edge of the measurement signal outputted from the detector circuit; and a delay measuring circuit configured to receive the change pulse signal outputted from the timing generating circuit, to receive an edge detection signal outputted from the edge detection circuit, and to measure a delay of a time for which the laser beam with an oscillation wavelength changed based on the change pulse signal reaches the detector circuit after the change pulse signal is outputted from the timing generating circuit, wherein the timing generating circuit is configured to delay a time for outputting data from the data acquisition circuit to the processor based on the delay of time outputted from the delay measuring circuit.

The detector circuit may include a light receiving element, a variable gain amplifier and an A/D converter, and the data acquisition circuit may include an integrator and a memory.

In the exemplary embodiment of the invention, it is possible to achieve a laser gas analysis apparatus in which a total delay of a system including delays caused by user's environment is measured and data are inputted to the processor based on the delay of a time so that the time delay can be cancelled.

BRIEF DESCRIPTION OF THE DRAWINGS

The above and other aspects of the present invention will become more apparent from the following description of exemplary embodiments, taken in conjunction with the accompanying drawings of which.

DETAILED DESCRIPTION

Figure 1:
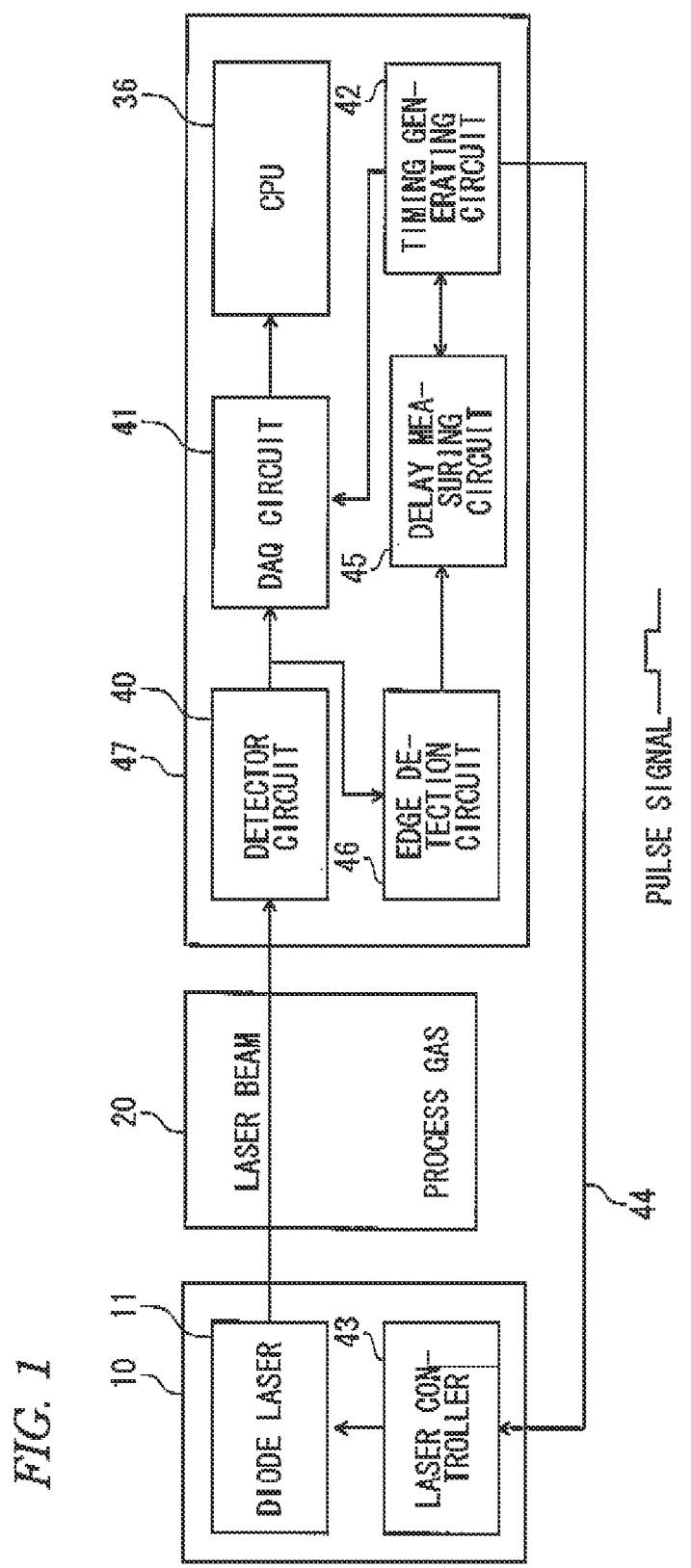
FIG. 1 is a block diagram showing a laser gas analysis apparatus according to an embodiment of the invention.

An exemplary embodiment of the invention will be described below in detail with reference to the drawings. FIG. 1 is a block diagram showing a laser gas analysis apparatus according to an embodiment of the invention. In FIG. 1, parts common with those in the related-art example shown in FIG.

Figure 3:
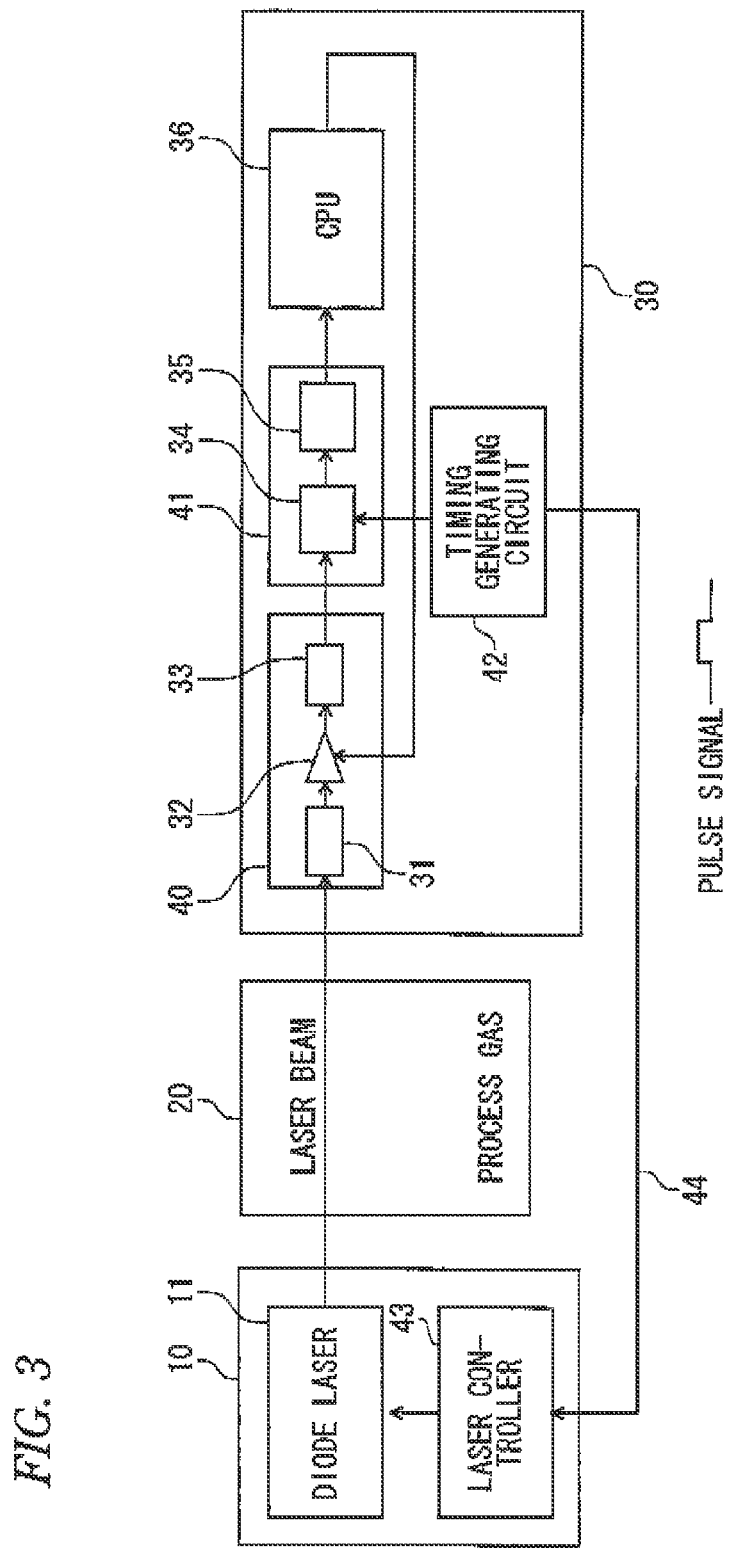
FIG. 3 is a block diagram showing a related-art laser gas analysis apparatus using the TDLAS method.
Figure 4A:
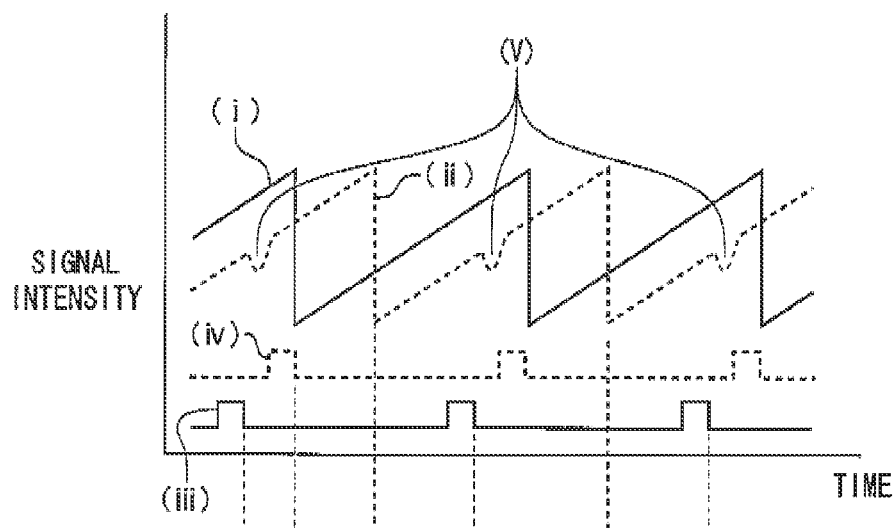
FIGS. 4A and 4B are graphs showing a timing sequence of the related-art laser gas analysis apparatus.
Figure 4B:
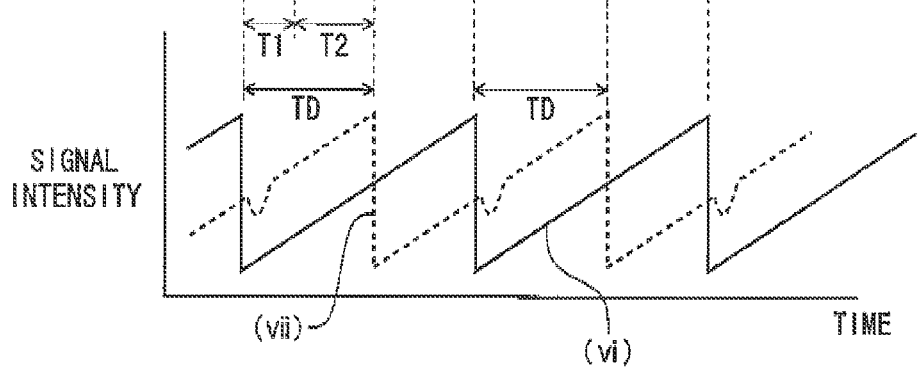

3 are referred to by the same numerals correspondingly. FIG. 1 is different from FIG. 3 in that a timing generating circuit, a delay measuring circuit and an edge detection circuit receiving an output from a detector circuit are provided.

In FIG. 1, a diode laser 11 provided as a semiconductor laser in a light source unit 10 emits a laser beam into an atmosphere of process gas 20 in the same manner as in the related-art. On this occasion, the oscillation wavelength of the laser beam is changed at a narrow band including an absorption wavelength in order to obtain the area of an absorption spectrum of a target component to be measured in the process gas 20.

The laser beam transmitted through the atmosphere of the process gas 20 is inputted to a detector circuit 40, which is provided with the same configuration as that in the related art, in a detection unit 47, and converted into a digital signal. More specifically, the detector circuit 40 includes a light receiving element, a variable gain amplifier and an A/D converter (See FIG. 3). The signal from the detector circuit 40 is inputted to a DAQ circuit 41, in which noise contained in the measurement signal is removed in order to smooth the signal in the same manner as in the related-art. More specifically, the DAQ circuit 41 includes an integrator and a memory (See FIG. 3). The resulting signal is then supplied to a CPU 36. The CPU 36 performs an arithmetic process for analysis of the concentration of the process gas etc. based on the measurement signal from which the noise has been removed.

So far the configuration is the same as that in the related-art. According to the embodiment, however, a delay measuring circuit 45 to which a pulse signal of a timing generating circuit 42 is inputted and an edge detection circuit 46 are provided. The delay measuring circuit 45 includes a counter, which begins to count as soon as a change pulse signal for changing the oscillation wavelength of the laser beam to be emitted from the diode laser is inputted from the timing generating circuit 42 to the delay measuring circuit 45.

On the other hand, the timing generating circuit 42 outputs, to a laser controller 43, the change pulse signal for changing the oscillation wavelength of the laser beam to be emitted from the diode laser. The laser controller 43 controls the diode laser 11 to change the oscillation wavelength of the laser beam based on the change pulse signal sent to the laser controller 43 through a sync cable 44, and a laser beam having the changed oscillation wavelength is emitted from the diode laser 11 and then is transmitted through the process gas 20 and inputted to the detector circuit 40.

An output of the detector circuit 40 is supplied not only to the DAQ circuit 41 but also to the edge detection circuit 46. The edge detection circuit 46 detects an edge (measurement start point) of the measurement signal detected by the detector circuit 40. An output from the edge detection circuit 46 suspends the count of the counter which has started in the delay measuring circuit 45. As a result, the delay measuring circuit 45 can measure a delay of a time for which the laser beam with the oscillation wavelength changed based on the change pulse signal reaches the detector circuit 40 after the change pulse signal is outputted from the timing generating circuit 42. The delay measuring circuit 45 sends the delay time to the timing generating circuit 42. The timing generating circuit 42 outputs a timing pulse signal corresponding to the delay time to the DAQ circuit 41 and the signal from the DAQ circuit 41 is inputted to the CPU 36 based on the timing pulse signal.

Figure 2:
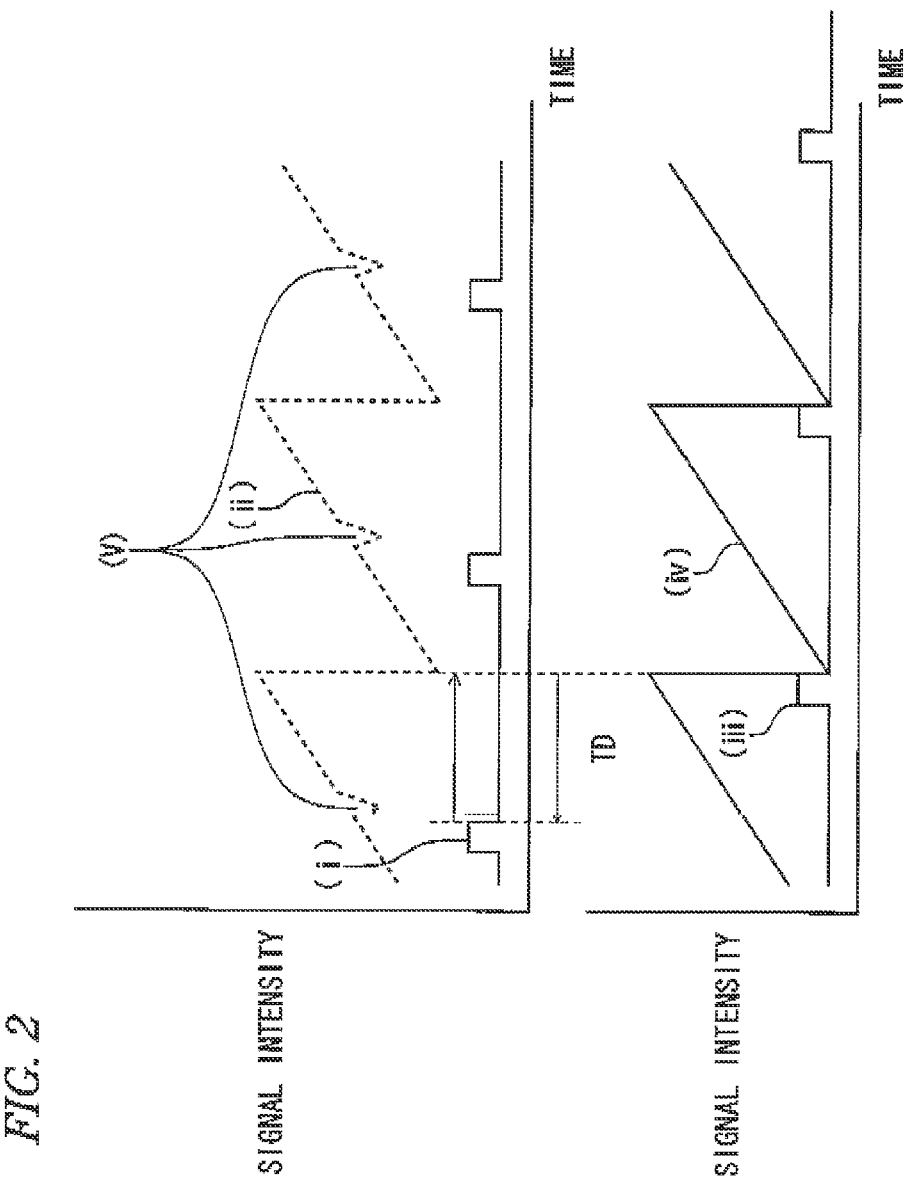
FIG. 2 is a graph showing a timing sequence of the laser gas analysis apparatus.

FIG. 2 is a graph showing a timing sequence of the laser gas analysis apparatus. The vertical axis designates signal intensity, and the horizontal axis designates time.

In FIG. 2, a solid line (i) designates the change pulse signal (output from the timing generating circuit), and a broken line (ii) designates a signal inputted to the DAQ circuit. A solid line (iii) designates a timing pulse signal outputted from the timing generating circuit 42 to the DAQ circuit 41 with a time delay TD. A solid line (iv) designates a signal inputted to the DAQ circuit without absorption by the process gas. Recesses (v) expressed in the broken line (ii) designate wavelength portions absorbed by the process gas.

According to the configuration, a total delay of the system including delays caused by user's environment is measured so that a signal can be inputted to the CPU based on the total delay. It is therefore possible to achieve a laser gas analysis apparatus which can perform accurate analysis.

In the description, a specific preferred embodiment is merely shown for the purpose of illustration and exemplification of the invention. For example, a plurality of counters may be provided in the edge detection circuit 46 and the delay measuring circuit 45 so that a change pulse signal outputted from the timing generating circuit 42 and received by the laser controller 43 can suspend the counters of the edge detection circuit 46 and the delay measuring circuit 45 directly through the sync cable. Thus, a delay T1 can be obtained, and a delay 12 can be also obtained based on a difference between T1 and TD. The sync cable length or the optical path length may be also obtained by use of a highly accurate and high-speed clock for the counters.

While certain embodiments have been described, these embodiments have been presented by way of example only, and are not intended to limit the scope of the invention. Indeed, the novel apparatus described herein may be embodied in a variety of other forms; furthermore, various omissions, substitutions and changes in the form of the apparatus, described herein may be made without departing from the sprit of the invention. The accompanying claims and their equivalents are intended to cover such forms or modifications as would fall within the scope and sprit of the invention

What is claimed is:

1. A laser gas analysis apparatus comprising:
    a light source unit including a semiconductor laser configured to emit a laser beam into process gas and a laser controller configured to control an oscillation wavelength of the laser beam;
    a detector circuit configured to detect the laser beam transmitted through the process gas;
    a data acquisition circuit configured to receive a measurement signal outputted from the detector circuit and to remove noise contained in the measurement signal;
    a processor configured to receive data outputted from the data acquisition circuit and to compute concentration of the process gas;
    a timing generating circuit configured to output, to the laser controller, a change pulse signal for changing the oscillation wavelength of the laser beam and to output, to the data acquisition circuit, a timing pulse signal for outputting data to the processor;
    an edge detection circuit configured to detect an edge of the measurement signal outputted from the detector circuit; and
    a delay measuring circuit configured to receive the change pulse signal outputted from the timing generating circuit, to receive an edge detection signal outputted from the edge detection circuit, and to measure a delay of a time for which the laser beam with an oscillation wavelength changed based on the change pulse signal reaches the detector circuit after the change pulse signal is outputted from the timing generating circuit, wherein the timing generating circuit is configured to delay a time for outputting data from the data acquisition circuit to the processor based on the delay of time outputted from the delay measuring circuit.

2. The laser gas analysis apparatus according to claim 1, wherein:

the detector circuit includes a light receiving element, a variable gain amplifier and an A/D converter, and the data acquisition circuit includes an integrator and a memory.

* * * * *